United States Patent [19]

Murphy

[11] Patent Number: 5,556,755

[45] Date of Patent: Sep. 17, 1996

[54] **METHOD FOR DETECTING *BRANHAMELLA CATARRHALIS***

[75] Inventor: Timothy F. Murphy, East Amherst, N.Y.

[73] Assignee: The Research Foundation of State University of New York, Amherst, N.Y.

[21] Appl. No.: 129,719

[22] Filed: Sep. 29, 1993

[51] Int. Cl.$^6$ .............................. C12Q 1/68; C12P 19/34; C07H 21/04; C12N 15/00

[52] U.S. Cl. ........................... 435/6; 435/91.1; 435/91.2; 435/871; 536/23.7; 536/24.32; 536/24.33; 536/25.3; 935/77; 935/78

[58] Field of Search ........................ 435/6, 91.1, 91.2, 435/871; 536/23.7, 24.32, 24.33, 25.3; 935/8, 9, 77, 78

[56] References Cited

U.S. PATENT DOCUMENTS

| | | |
|---|---|---|
| 4,683,195 | 7/1987 | Mullis et al. ................................. 435/6 |
| 5,030,556 | 7/1991 | Beaulieu et al. ............................. 435/6 |

OTHER PUBLICATIONS

Bartos and Murphy, "Comparison of the Outer Membrane Proteins of 50 strains of *Branhamella catarrhalis*", Journal of Infectious Diseases, vol. 158, No. 4, 1988, pp. 761–765.

Sarwar et al., "Characterization of an Antigenically Conserved Heat–Modifiable Major Outer Membrane Protein of *Branhamella catarrhalis*", Infection and Immunity, vol. 60, No. 3, pp. 804–809.

Sequence comparison printout; Registry No. 129187–22–0.

Sommer and Tantz, *Nucleic Acids Research*, vol. 17, No. 16, 1989, p. 6749.

*Primary Examiner*—Stephanie W. Zitomer
*Assistant Examiner*—Bradley L. Sisson
*Attorney, Agent, or Firm*—Hodgson, Russ, Andrews, Woods & Goodyear

[57] ABSTRACT

Compositions comprising outer membrane protein "CD", and peptides thereof, of *Branhamella catarrhalis* are described. Additionally, nucleotide sequences encoding the protein or peptide are disclosed, as well as recombinant vectors containing these sequences. Protein or peptide can be produced from host cell systems containing these recombinant vectors. Peptides can also be chemically synthesized. Disclosed are the uses of the protein and peptides as antigens for vaccine formulations, and as antigens in diagnostic immunoassays. The nucleotide sequences are useful for inserting into a viral vector in constructing a recombinant viral vaccine. Also described is the use of nucleotide sequences related to the gene encoding CD as primers and/or probes in molecular diagnostic assays for the detection of *B. catarrhalis*.

10 Claims, 3 Drawing Sheets

METHOD FOR DETECTING *BRANHAMELLA CATARRHALIS*

This invention was made with government support under grant A128304 awarded by the National Institutes of Health. The government has certain rights in the invention.

FIELD OF INVENTION

The present invention relates to compositions comprising a protein, and peptides thereof, associated with the outer membrane of *Branhamella cattarrhalis*. More particularly, the invention is directed to compositions of a protein, and peptides thereof, related to an outer membrane protein, "CD", of apparent molecular mass of about 55,000 to 60,000 daltons found in *B. cattarrhalis*. Also disclosed is methods for preparing CD and CD peptides using recombinant DNA and/or biochemical techniques. Related thereto, disclosed is the DNA sequence encoding CD, and vectors useful in directing the expression of CD and CD peptides.

The proteins and peptides are used as immunogens in vaccine formulations for active immunization; and can be used to generate protein-specific and peptide-specific antisera useful for passive immunization, and as reagents for diagnostic assays. The nucleotide sequences disclosed provide for the synthesis of corresponding oligonucleotides which can be used as reagents in diagnostic assays directed to the detection of *B. cattarrhalis* genetic material.

BACKGROUND OF THE INVENTION

*Branhamella catarrhalis* (also known as *Moraxella catarrhalis*) is an important human respiratory tract pathogen. *B. catarrhalis* is the third most common cause of otitis media in infants and children, after *Streptococcus pneumoniae* and nontypeable *Haemophilus influenzae*, as documented in studies in which tympanocentesis has been used to establish the etiologic agent Murphy, 1989, Pediatr. Infect. Dis. J. 8:S75–S77). *B. catarrhalis* is a common cause of sinusitis and conjunctivitis in both children and adults (See for example, Bluestone, 1986, Drugs 31:S132–S141; Brorson et al., 1976, Scand. J. Infect. Dis. 8:151–155; and Romberger et al., 1987, South. Med. J. 80:926–928); and is an important cause of lower respiratory tract infections in adults with chronic bronchitis and chronic obstructive pulmonary disease (Murphy et al., 1992, Am. Rev. Respit. Dis. 146:1067–1083; Catlin, 1990, Clin. Microbiol. Rev. 3:293–320). Additionally, *B. catarrhalis* can cause pneumonia, endocarditis, septicemia, and meningitis in immunocomprised hosts (Cocchi et al., 1968, Acta Paediatr. Scand. 57:451–3; Douer et al., 1977, Ann. Intern. Med. 86:116–119; McNeely et al., 1976, Am. Rev. Respit. Dis. 114:399–402).

Since recurrent otitis media is associated with substantial morbidity, there is interest in identifying strategies for preventing these infections. One such approach is the development of vaccines. An effective vaccine for preventing bacterial otitis media would need to include antigens which would generate protection against infection by *S. pneumoniae*, nontypeable *H. influenzae* and *B. catarrhalis*. Indeed, vaccine development for the pneumococcus and nontypeable *H. influenzae* are progressing such that potentially protective antigens have been identified and are currently undergoing testing (See for example, Murphy et al., U.S. Pat. No. 5,173,294; and Vella et al., 1992, Infect. Immun. 60:4977–4983). As these vaccines are developed and used more widely, the relative importance of *B. catarrhalis* as a cause of otitis media will increase in the next decade.

Besides infants and children benefitting from a vaccine to prevent otitis media caused by *B. catarrhalis*, adults with chronic obstructive pulmonary disease, and immunocompromised children and adults would benefit from a vaccine to prevent infections caused by *B. catarrhalis*.

Bacterial components which have been investigated as potential vaccine antigens include polysaccharides, lipopolysaccharides or modifications thereof, and outer membrane proteins. In general, as exemplified by the type b capsular polysaccharide of *H. influenzae*, polysaccharide antigens have been shown to be a poor immunogen in children under the age of 18 months. Active immunization with lipopolysaccharide (LPS) is unacceptable due to its inherent toxicity. The pathophysiologic effects of LPS may include fever, leucopenia, leucocytosis, the Shwartzman reaction, disseminated intravascular coagulation, and in large doses, shock and death. In general, proteins are immunogenic in infants around three months of age. Thus, outer membrane proteins are being investigated as possible vaccine antigens.

while recent studies have begun to focus on outer membrane proteins of *B. catarrhalis*, little is known about the antigenic and molecular structure of these proteins. Studies of purified outer membranes by SDS-PAGE have revealed a rather homogeneous pattern among strains of the bacterium (Bartos and Murphy, 1988, J. Infect. Dis. 158:761–765). Eight major outer membrane proteins, designated by the letters A–H, have been identified (Murphy et al., 1989, Microbial Pathogen. 6:159–174; Bartos et al., 1988, J. Infect. Dis. 158: 761–765). Outer membrane proteins C and D differ slightly in apparent molecular mass, and thus appear as a doublet on SDS-PAGE electrophoresis. Monoclonal antibodies have been developed to *B. catarrhalis* resulting in two monoclonal antibodies, 7D6 and 5E8, which recognized both proteins C and D (Sarwar et al., 1992, Infect. Immun. 60:804–809). Prior to the development of the present invention, it was unknown whether this doublet represented a single protein (CD) with two stable conformations, or whether C and D are two closely related proteins encoded by different genes (Sarwar et al., supra). Proteins C and D are of interest, particularly for vaccine development, because these proteins express at least one conserved epitope on the surface of intact *B. catarrhalis* (Satwar et al., 1992, supra).

Hence, with the increasing recognition of *B. catarrhalis* as an important bacterial pathogen, there is a need for a vaccine that is immunogenic in children and adults. Such a vaccine would have to be directed to a bacterial component which has a surface-exposed epitope on intact bacteria, wherein the epitope is conserved amongst strains of *B. catarrhalis*.

SUMMARY OF THE INVENTION

The present invention is directed to a protein and peptides related to an outer membrane protein having an apparent molecular mass of about 55,000 to 60,000 daltons of *B. catarrhalis*, wherein the protein was formerly thought to be two related proteins, C and D, but which through recombinant DNA techniques disclosed herein, is now known to be one protein, CD, which is heat modifiable resulting in the appearance of two proteins differing by migration in SDS gels. The CD protein, and peptides thereof (herein termed "CD peptides"), of the present invention may be used as immunogens in vaccine formulations; or as an antigen in diagnostic immunoassays directed to detection of *B. catarrhalis* infection by measuring an increase in serum titer of *B. catarrhalis*-specific antibody. Also, CD protein and CD peptides of the present invention may be used to generate CD-specific antibody which may be useful for passive immunization and as reagents for diagnostic assays directed to detecting the presence of *B. catarrhalis* in clinical specimens. CD peptides can be obtained by chemical synthesis, purification from *B. catarrhalis*, or from recombinant vector expression systems using the nucleic acid sequences disclosed herein.

The present invention also provides methods for molecular cloning of the gene encoding CD, and gene fragments encoding CD peptides. The nucleic acid sequences of the present invention can be used in molecular diagnostic assays for *B. catarrhalis* genetic material through nucleic acid hybridization, and including the synthesis of CD sequence-specific oligonucleotides for use as primers and/or probes in amplifying, and detecting amplified, nucleic acids. Additionally, the gene encoding CD, or one or more gene fragments encoding CD peptides, may be incorporated into a viral vaccine comprising a recombinant virus which is engineered to produce one or more immunogenic epitopes of CD by itself, or in combination with immunogenic epitopes of other pathogenic microorganisms.

FIG

Figure 1:
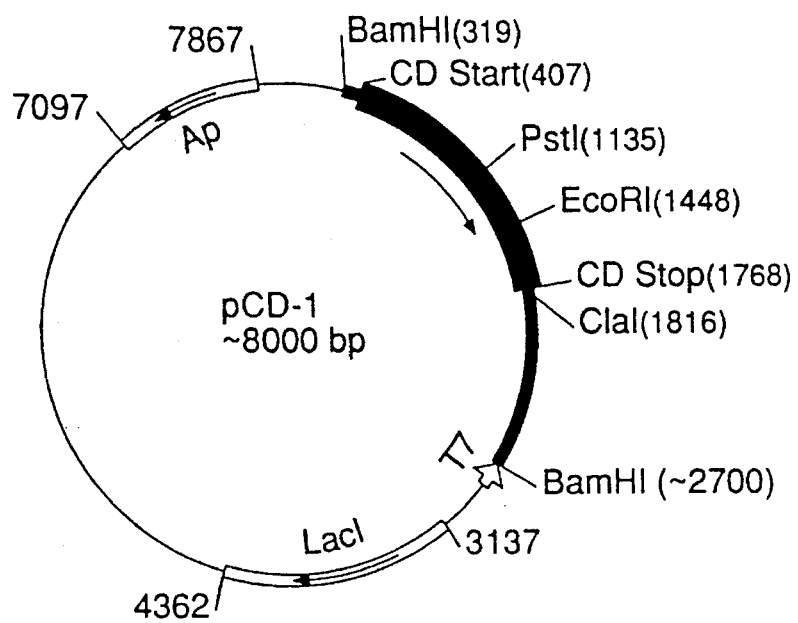
FIG. 1 represents a map of plasmid pCD-1, constructed from pET11b and a 2.4 kb fragment containing the gene which encodes CD. The shaded region represents the DNA insert and the thicker shaded region represents the CD gene. Abbreviations used are as follows: Ap: ampicillin resistance coding region; Lac: lac operon; bp: base pairs.

Embodiment B—Conservation of the gene encoding CD amongst *B. catarrhalis* strains;

Embodiment C—Methods for using CD-specific nucleotide sequences in molecular diagnostic assays for the detection of *B. catarrhalis;*

Embodiment D—Characterization of CD including generation of CD peptides;

Embodiment E—Methods for using CD, or CD peptides, in diagnostic immunoassays;

Embodiment F—Methods and compounds for vaccine formulations related to CD and CD peptides.

Embodiment A

Molecular cloning and sequencing of the gene encoding CD, and vectors expressing CD epitopes.

The strategy used was to isolate genomic DNA from *B. catarrhalis*, cleave the isolated DNA into fragments, construct a genomic library comprising insertion of the fragments into an expression vector, introduce the recombinant vectors into the appropriate host cell, and immunoscreen for host cell clones expressing CD-specific epitopes by using CD-specific antisera. *Branhamella catarrhalis* strain 25240, obtained from the American Type Culture Collection (ATCC) was used as the source of bacterial genomic DNA. *B. catarrhalis* was grown on chocolate agar plates at 37° C. in 5% $CO_2$ or in brain heart infusion broth. *Escherichia coli* (*E. coli*) Y1090 was used as the host strain for the bacteriophage lambda gt11 genomic library. Depending on the circumstances, *E. coli* was grown in LB broth, or on LB agar containing 50 µg/ml of ampicillin. Monoclonal antibodies used for immunoscreening clones included 5E8 and 7D6 which recognize different epitopes on the CD outer membrane protein of *B. catarrhalis* (Earwar et al., supra). Antibody 5E8 is an IgM and recognizes an epitope which is exposed on the surface of the intact bacterium. Antibody 7D6 is an IgG2a and binds an epitope which is not accessible on the bacterial surface.

A lambda gt11 library was constructed with genomic DNA of *B. catarrhalis* 25240 using previously described methods (Nelson et al., 1988, Infect. Immun. 56:128–134). Genomic DNA fragments of 2 to 8 kilobases (kb) in size were eluted from an agarose gel and ligated to phage arms. A portion of the library was introduced into *E. coli* Y1090 and the resultant plaques were transferred onto nitrocellulose discs and immunoscreened with monoclonal antibodies 5E8 and 7D6. After incubation with the monoclonal antibodies overnight, the discs were incubated with protein A peroxidase and anti-mouse IgM peroxidase conjugate, with subsequent substrate development, to identify immunoreactive plaques. Screening of a total of approximately 554,000 plaques yielded a clone which contained a 387 base pair insert expressing the epitopes recognized by antibodies 7D6 and 5E8. Nucleotide sequence analysis of the insert contained within this clone showed an open reading frame with no start or stop codons (SEQ ID No. 1). The nucleotide sequence of this clone corresponds to nucleotides 775–1160 of SEQ ID No. 14 that contains the whole gene sequence encoding CD. The peptide produced by this clone, as shown in SEQ ID No. 1, corresponds to amino acids 203–331 in the mature protein depicted in SEQ ID No. 14.

Since several rounds of screening of the lambda gt11 genomic library yielded a small fragment of the CD gene, an EMBL3 library was constructed with genomic DNA of *B. catarrhalis* 25240 with insert sizes of approximately 9 to 23 kb. This library was immunoscreened with monclonal antibodies 5E8 and 7D6. The EMBL3 genomic library was constructed with methods known in the art (Ausubel et al., 1989, Current Protocols in Molecular Biology, published by John Wiley and Sons) and according to the recommendations of the manufacturer (Stratagene, LaJolla, Calif.). Briefly, genomic DNA of *B. catarrhalis* 25240 was purified using SDS, proteinase K and CTAB. The purified genomic DNA was partially digested with Sau3A to generate varying-size fragments. The DNA fragments were separated by sucrose gradient centrifugation on a 10 to 40% sucrose gradient. The fractions containing fragments of approximately 9 to 23 kilobases in size were dephosphorylated using calf alkaline phosphatase, and precipitated with ethanol to prepare for ligation to EMBL3 arms. Approximately 0.7 µg of these genomic DNA fragments were ligated to 1 µg of EMBL3 arms by using T4 DNA ligase. The ligated phage arms and inserts were packaged into phage and the titer of the library was determined by plating on *E. coli* P2 392, the host strain for the lambda EMBL3 genomic library. The EMBL3 genomic library was immunoscreened with monoclonal antibodies 5E8 and 7D6 as described above.

Immunoscreening of approximately 3500 plaques from the EMBL library yielded a single reactive plaque, designated clone 5. The purified clone was assayed with antibodies 5E8 and 7D6 individually and was reactive with both antibodies. Control experiments showed that the protein A and anti-mouse IgM peroxidase conjugates did not bind to plaques of clone 5.

Phage DNA from clone 5 was purified and digested with SalI to excise the insert. Agarose gel electrophoresis revealed that clone 5 had an insert of 13 kb. The insert was digested with several restriction enzymes and a Southern blot assay was performed. The blot was probed with an oligonucleotide corresponding to DNA sequence from the 387 bp fragment of the CD gene recovered from the lambda gt11 library. The gene encoding CD was determined to be localized to a 2.4 kb NcoI-SalI fragment. The 2.4 kb fragment was subcloned into the BamH1 site of pET11b (Novagen, Madison, Wis.) by ligating BamH1 linkers onto the insert after its ends were made blunt with Klenow DNA polymerase. The resulting plasmid, which contained a 2.4 kb insert, was called pCD1 (FIG. 1). Plasmid pET11b, and recombinant pCD1 were propagated in *E. coli* HB101 on LB agar containing 50 µg/ml of ampicillin. A whole cell lysate of transformants containing pCD1 was subjected to SDS-PAGE and immunoblot assay with antibodies 7D6 and 5E8. The results indicate that pCD1 encodes a full length CD protein which is reactive with both antibodies.

Dideoxy sequencing of both strands of 1727 bp of the 2.4 kb insert of pCD1 was performed with the aid of additional oligonucleotides synthesized to correspond to sequence at appropriate intervals within the insert such as represented by SEQ ID Nos. 2–13. An open reading frame of 453 amino acids, which represents a protein of 48,277 daltons, was identified (SEQ ID No. 14). A strong transcriptional terminator was present beginning 54 bp downstream of the stop codon.

Figure 2:
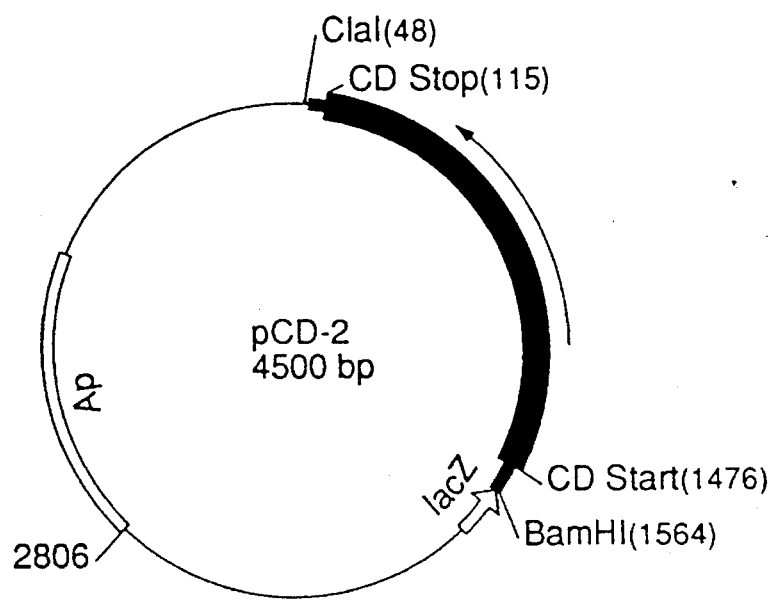
FIG. 2 represents a map of plasmid pCD-2, constructed from pGEM7zf— and a 1.5 kb fragment containing the gene which encodes CD. The shaded region represents the DNA insert and the thicker shaded region represents the gene encoding CD. Abbreviations used are as follows: Ap: ampicillin resistance coding region; Lac: lac operon; bp: base pairs.
Figure 3:
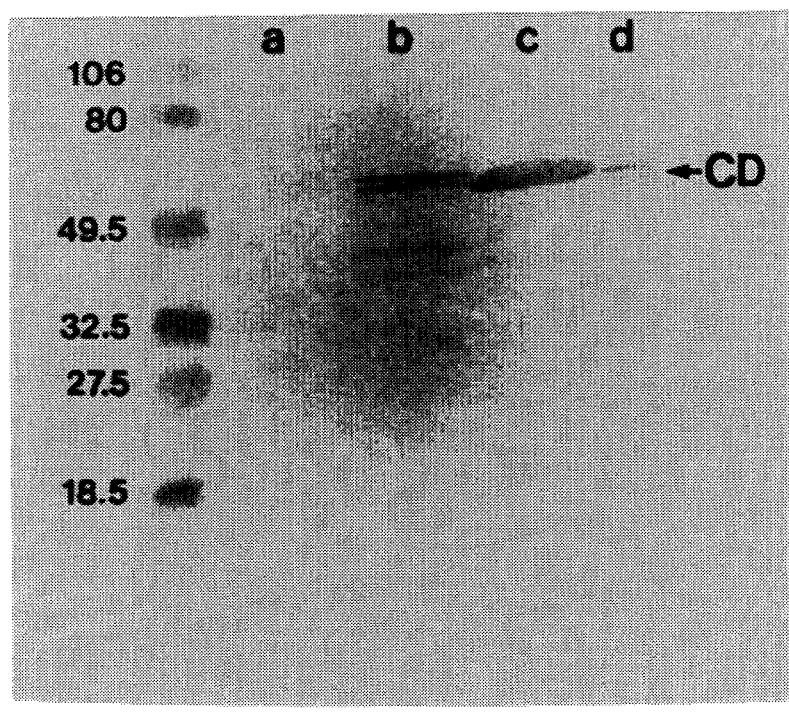

The calculated molecular mass of the mature protein (45,788 daltons) differed significantly from the apparent molecular mass of OMP CD observed in SDS-PAGE (60,000 or 55,000, daltons in reduced or nonreduced form, respectively). Therefore, a plasmid containing the open reading frame without downstream sequence was constructed to determine whether expression of the reading frame would yield a full size CD protein. A ClaI site is located 48 bp downstream of the open reading frame. A BamH1-ClaI DNA fragment of 1558 bp containing the putative CD gene was subcloned into pGEM7zf— (Promega Corp., Madison, Wis.) in constructing new plasmid pCD2 (FIG. 2). By immunoblot assay, shown in FIG. 3 (lane b), *E. coli* transformants containing pCD2 express a full-size CD protein. In addition, the immunoblot assay shows that the CD gene product migrates as a doublet (lane b), indicating that both bands represent products of a single gene rather than representing two related proteins produced by their respective genes.

Thus, this embodiment illustrates that nucleotide sequences encoding CD or portions thereof, can be inserted into, and expressed by various vectors including phage vectors and plasmids. Successful expression of the protein and peptides requires that either the insert comprising the gene or gene fragment, or the vector itself, contain the necessary elements for transcription and translation which is compatible with, and recognized by the particular host system used for expression. Host systems which can be utilized include bacteria, yeast, fungi, insect cell lines, and mammalian cell lines. Using methods known in the art of molecular biology, including methods described above, various promoters and enhancers can be incorporated into the vector or gene sequence to increase the expression of CD protein and CD peptides, provided that the increased expression of the protein or CD peptide is compatible with the particular host cell system used. Recombinant CD protein and CD peptides can be purified for use as an immunogen in subunit vaccine formulations; and as an antigen for diagnostic assays or for generating *B. catarrhalis*-specific antisera of therapeutic and/or diagnostic value.

Embodiment B

Conservation of the gene encoding CD amongst *B. catarrhalis* strains.

For the nucleotide sequences of the present invention to be useful in diagnostic assays, the gene encoding CD must be highly conserved amongst strains of *B. catarrhalis*. In addition, a highly conserved gene indicates that the protein sequence is also highly conserved. For a bacterial protein or peptide to be useful as an antigen in subunit vaccine formulations against infection caused by *B. catarrhalis*, the protein or peptide must contain epitopes that are both immunogenic, and conserved amongst strains of *B. catarrhalis*. To determine the degree of conservation of the CD gene among strains of *B. catarrahlis*, genomic DNA was purified and analyzed from 30 isolates recovered from diverse clinical and geographic sources (Table 1). Analysis involved restricting the DNA into fragments, and probing with an oligonucleotide of a sequence which includes, but is not limited to, those represented by SEQ ID Nos. 2–13.

TABLE 1

Sources of isolates of *Branhamella catarrhalis*

| Clinical Site | Number of Isolates |
| --- | --- |
| sputum | 15 |
| middle ear fluid[1] | 7 |
| nasopharynx | 3 |
| eye | 2 |
| adenoid | 1 |
| blood | 1 |
| ATCC[2] | 1 |

[1]Middle ear fluid was obtained by tympanocentesis.
[2]American Type Culture Collection.

The genomic DNA from 30 strains (including 25240) of *B. catarrhalis* was purified. A volume of 30 ml of brain heart infusion broth was inoculated with a single colony and incubated at 37° C. with shaking overnight. Cells were harvested by centrifugation at 2200×g for 10 minutes at 4° C. The pelleted cells were suspended in 7 ml of TE buffer (0.01M tris, pH 8, 0.001M EDTA, pH 8.0). EDTA was added to 0.005M and SDS was added to 0.5%. The suspension was incubated at 60° for 30 minutes. Proteinase K was added to 200 µg/ml followed by incubation at 37° C. for approximately 24 hours. The sample was extracted sequentially with equal volumes of phenol, followed by phenol/chloroform at a 1:1 ratio, followed by chloroform. A 10% volume of 3M sodium acetate (pH 5.2) was added and DNA was precipitated by the addition of cold ethanol equivalent to 80% of the volume. Genomic DNA precipitated and was removed by "spooling" with a pasteur pipette. The DNA was washed in 70% ethanol and dissolved in 0.05M tris, pH 8.0. RNase was added to a final concentration of 40 µg/ml and the sample was incubated at 37° for 30 minutes. EDTA was added to a concentration of 0.001M. The sample was extracted sequentially with phenol and chloroform and ethanol precipitated. The purified DNA was dissolved in 0.01M Tris, 0.1 mM EDTA, pH 8.0.

An aliquot equivalent to 10 µg of DNA was digested with EcoRI or PstI with a reaction volume of 0.5 ml. The resulting DNA fragments were separated by agarose gel electrophoresis and transferred to a charged nitrocellulose membrane by Southern blot. The Southern blots were probed with two oligonucleotide probes corresponding to sequences upstream and downstream of the EcoRI site within the gene encoding CD (this Eco RI site is depicted in FIG. 1). The oligonucleotides had been end-labeled with [$^{32}$P]ATP by using T4 polynucleotide kinase before use as probes. Hybridizations were carried out at 37° C. and washes were performed at 48° C. The hybridization and wash buffers were described previously (Nelson et al., supra). Autoradiography was performed at −70° C.

Figure 4:
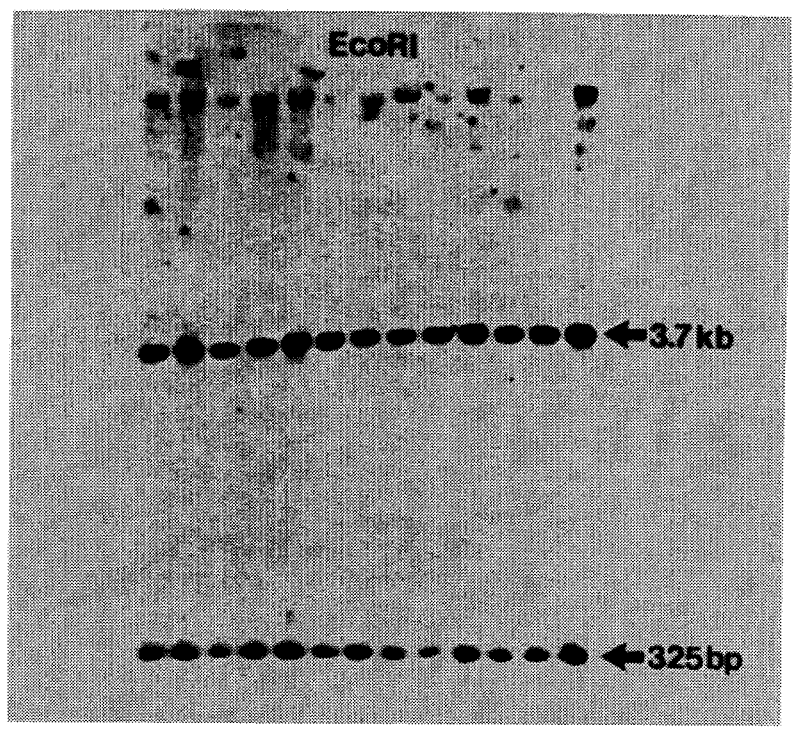

All 30 strains produced an identical pattern of bands, including a 325 bp band representing the fragment between the EcoRI site within the gene and the site just downstream of the gene. In addition, all 30 strains showed a 3.7 kb band representing a fragment upstream of the CD gene. This pattern is exemplified by FIG. 4 showing the Southern blot assay of 13 strains.

Figure 5:
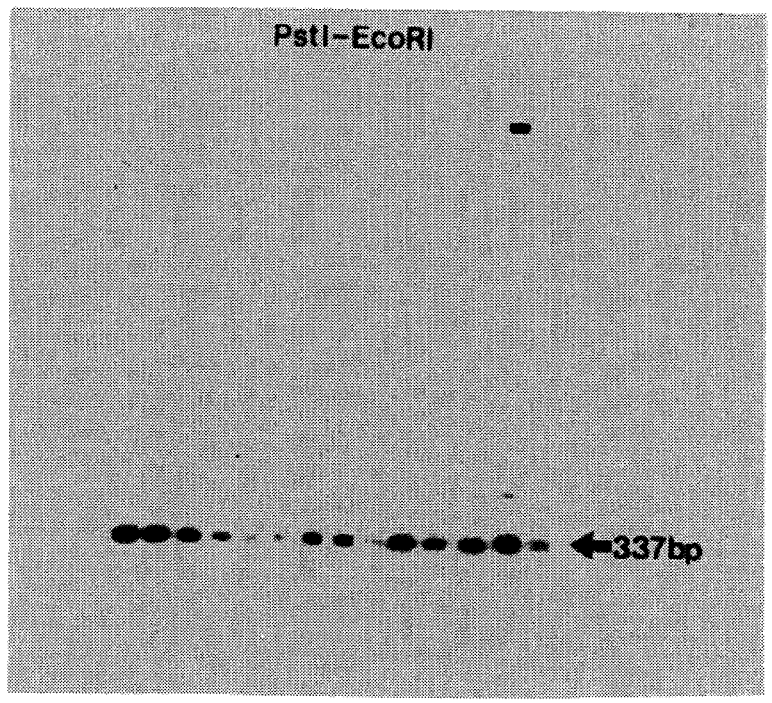

To further analyze the molecular conservation of the CD gene, genomic DNA from the same 30 strains was digested with EcoRI and PstI and probed with oligonucleotides. FIG. 1 shows that the gene encoding CD, isolated from strain 25240, has a PstI site near the center of the gene and that digestion with EcoRI and PstI will yield a DNA fragment of 337 base pairs. Southern blot assays showed that genomic DNA from 30 of 30 strains of *B. catarrhalis* yielded an identical 337 bp fragment which hybridized with an oligonucleotide corresponding to sequence in the the gene encoding CD isolated from strain 25240. This pattern is exemplified by FIG. 5 showing the Southern blot assay of 13 strains. These findings indicate that the gene encoding CD is highly conserved amongst strains of *B. catarrhalis*, and therefore the nucleotide sequences described herein have applications for diagnostic and vaccine use.

Embodiment C

Methods for using CD-specific nucleotide sequences in molecular diagnostic assays for the detection of *B. catarrhalis*.

Because of the conservation of the gene encoding CD, as disclosed in Embodiment B, the nucleic acid sequences of the present invention can be used in molecular diagnostic assays for detecting *B. catarrhalis* genetic material. In particular, CD sequence-specific oligonucleotides can be synthesized for use as primers and/or probes in amplifying, and detecting amplified, nucleic acids from *B. catarrhalis*. Recent advances in molecular biology have provided several means for enzymatically amplifying nucleic acid sequences. Currently the most commonly used method, PCR™ (polymerase chain reaction, Cetus Corporation) involves the use of Taq Polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA™ (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3$–$10^4$ organisms per specimen (1990, *Gene Probes for Bacteria*, eds. Macario and deMacario, Academic Press). Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the gene encoding CD of *B. catarrhalis*, and to probes which specifically hybridize with these amplified DNA fragments. By using the nucleic acid sequences of the present invention and according to the methods of the present invention, as few as one *B. catarrhalis* organism may be detected in the presence of 10 µg/ml extraneous DNA.

This embodiment is directed to species-specific oligonucleotides which can be used to amplify sequences of *B. catarrhalis* DNA, if present, from DNA extracted from clinical specimens including middle ear fluid, sputum, blood, and fluids from the nasopharynx, eye, and adenoid; and to subsequently determine if amplification has occurred. In one embodiment of the present invention, a pair of *B. catarrhalis*-specific DNA oligonucleotide primers are used to hybridize to *B. catarrhalis* genomic DNA that may be present in DNA extracted from a clinical specimen, and to amplify the specific segment of genomic DNA between the two flanking primers using enzymatic synthesis and temperature cycling. Each pair of primers are designed to hybridize only to the *B. catarrhalis* nucleotide sequences of the present invention to which they have been synthesized to complement; one to each strand of the double-stranded DNA. Thus, the reaction is specific even in the presence of microgram quantities of heterologous DNA. For the purposes of this description, the primer derived from the sequence of the positive (gene) strand of DNA will be referred to as the "positive primer", and the primer derived from the sequence of the negative (complementary) strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the *B. catarrhalis* DNA sequences, if present, results. Further identification of the amplified DNA fragment as being derived from *B. catarrhalis* DNA, may be accomplished by liquid hybridization. This test utilizes one or more labeled oligonucleotides as probes to specifically hybridize to the amplified segment of *B. catarrhalis* DNA. Detection of the presence of sequence-specific amplified DNA may be accomplished using any one of several methods known in the art such as a gel retardation assay with autoradiography. Thus, the nucleotide sequences of the present invention provide basis for the synthesis of oligonucleotides which have commercial applications in diagnostic kits for the detection of *B. catarrhalis*. In a related embodiment, the oligonucleotides used as primers may be labeled directly, or synthesized to incorporate label. Depending on the label used, the amplification products can then be detected, after binding onto an affinity matrix, using isotopic or colorimetric detection.

DNA may be extracted from a clinical specimens which may contain *B. catarrhalis* using methods known in the art. For example, cells contained in the specimen may be washed in TE buffer and pelleted by centrifugation. The cells then may be resuspended in 100µl of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% non-ionic, 0.045% Tween non-ionic detergent (Tween) 20™, and 60 µg/ml proteinase K. The sample is incubated at 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

The *B. catarrhalis* DNA may be amplified using any one of several protocols for amplifying nucleic acids by the polymerase chain reaction. In one mode of this embodiment, the gene encoding CD was amplified from 25 clinical isolates of *B. catarrhalis* using the following conditions. DNA to be amplified (≈1 µg of genomic DNA) was distributed in 0.5 ml microfuge tubes and the volume was adjusted to 50 µl by adding a reaction mixture comprising 0.2 mM dNTPs (dATP, dCTP, dGTP, dTTP), 0.25 µg of each positive and negative oligonucleotide primer, 1 unit of TaqI polymerase, TaqI 10×buffer (5 µl), 1 mM$MgCl_2$ (final concentration), and sterile distilled water to achieve the total volume. The TaqI polymerase is added to the reaction mixture just before use and is gently mixed, not vortexed. A layer of mineral oil, approximately 2 drops, is added to each tube and then the tubes are placed in the thermal cycle. Thirty to thirty-five cycles are generally sufficient for bacterial DNA amplification. One cycle consists of 1 minute at 95° C., 1 minute at 37° C., and 1 minute at 72° C. The first cycle includes a 1½ minute incubation at 95° C. to assure complete denaturation.

Oligonucleotides useful as primers or probes which specifically hybridize to the gene encoding CD of *B. catarrhalis* and used in DNA amplification and/or detection can be biochemically synthesized, using methods known in the art, from the nucleotide sequences disclosed in the present invention. The specificity of the oligonucleotides for *B. catarrhalis* can be checked by a gene-bank database (Genbank) search for each individual sequence. In general, the oligonucleotides should be selected for low G-C content. Pairs of primers that have been used for this embodiment to amplify the whole gene encoding CD include SEQ ID No. 15 (negative primer) and SEQ ID No. 16 (positive primer). Pairs of primers used to amplify the portion of the gene that encodes 5E8 and 7D6 epitopes include SEQ ID No. 17 (negative primer) and SEQ ID No. 18 (positive primer).

For detection purposes, the oligonucleotides of the present invention may be end-labeled with a radioisotope. Probe sequences, internal to the two primers used for amplification of the gene sequence, may be end-labeled using $T_4$ polynucleotide kinase and gamma $^{32}$p ATP. Twenty pMols of probe DNA in kinase buffer (50 mM Tris, pH 7.6, 10 mM $MgCl_2$, 5 mM dithiothreitol, 0.1 mM spermidine-HCl, 0.1 mM EDTA, pH 8.0) is mixed with 120 µCi of gamma $^{32}$p ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight at 37° C. The eluted probe is separated from the gel fragments by centrifugation using a chromatography prep column. Radioactivity of the probe is determined, by counting one microliter of the labeled probe on a glass fiber filter, by liquid scintillation. Such probe sequences may be chosen from any of the sequences identified as SEQ ID Nos. 2–13 provided the probe sequence is internal to the two primers used for amplification of the desired nucleotide sequence disclosed in the present invention.

Alternative methods known in the art may be used to improve the detection of amplified target sequences in accordance with the compositions and methods of the present invention. The sensitivity of detection of the amplified DNA sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternately, the amplified target sequences may be immobilized by hybridization to the corresponding probes of the target sequence wherein the probes have been affixed onto a matrix. Detection may be accomplished using an avidin conjugate containing an enzyme which can be used to visualize the complex with subsequent substrate development.

Embodiment D

Characterization of CD, including generation of CD peptides.

To confirm that the gene encoding CD had been identified, the amino terminus of the CD protein was determined. To identify the amino terminus of the CD protein, purified outer membrane of *B. catarrhalis* 25240 was subjected to SDS-PAGE and transferred to polyvinylidine difluoride membrane by electrophoretic blotting. The CD band was excised and the amino terminal sequence of the protein was determined by Edmund degradation, with the amino acids being analyzed by a microsequencer. The amino terminal sequence, G—V—T—V—S—P—L—L—L—G corresponded to amino acids 27 through 36 of the open reading frame of pCD1, indicating that CD has a 26 amino acid leader peptide. A hydrophobic 26 amino acid leader peptide is characteristic of bacterial OMPs whose leader peptides are cleaved by signal peptidase I (Oliver, 1985, Ann. Rev. Microbiol. 39:615–648).

To further establish that the gene encoding CD had been identified, the amino acid sequence deduced from the gene sequence was analyzed for the presence of methionine residues to predict the result of cyanogen bromide cleavage of the protein. The open reading frame corresponding to the mature protein contains four methionines indicating that cleavage with cyanogen bromide would yield five fragments. Cyanogen bromide cleavage of CD was accomplished by purifying outer membrane (Murphy et al., 1989, Infect. Immun. 57:2938–2941) and subjecting the outer membrane preparation to SDS-PAGE. The gel was stained with amido black so that the CD band could be visualized and excised from the gel. The gel slices (3–4 mm in length) were placed into the tubes of an electroeluter with 0.05M ammonium bicarbonate, 0.1% SDS. The protein was eluted, at 10 mA per tube until the gel slices were completely free of amido black (approximately 5 hours). The eluted protein was collected and an aliquot of 0.6 ml was precipitated by the addition of 2 ml of cold ethanol. The sample was centrifuged and the pellet was air dried. A volume of 0.4 ml of cyanogen bromide (200 mg/ml) in 70% formic acid was added to the pellet and the sample was incubated overnight at room temperature in the dark. A simultaneous control sample was incubated in 70% formic acid under identical conditions. The next day 1 ml of water was added and the samples were lyophilized. The lyophilized peptides were suspended in sample buffer and subjected to tricine gel electrophoresis.

Figure 6:
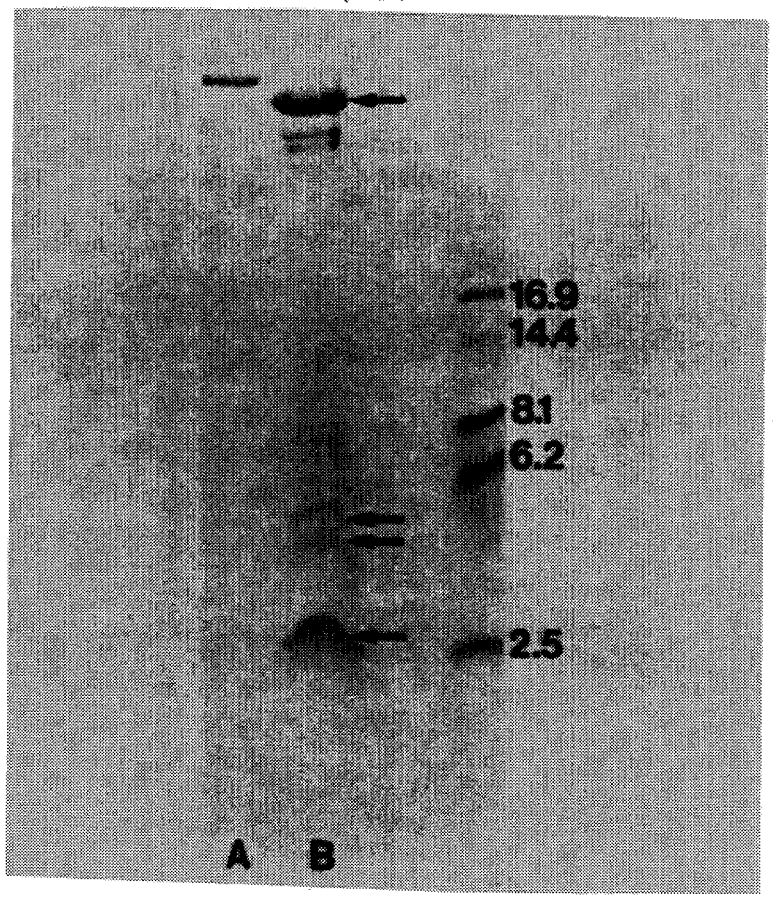

Table 2 shows the size of the fragments (CD peptides) predicted by the methionine sites in the open reading frame. FIG. 6 shows the actual fragments obtained from cyanogen bromide treatment of purified CD, as determined by the tricine polyacrylamide gel system of Lesse et al. (1990, J. Immunol. Methods 126: 109–117). The predicted and actual sizes of the cyanogen bromide cleaved fragments are in good agreement with the exception of the large fragment from the amino terminal region of the protein (Table 2).

TABLE 2

Cyanogen bromide cleavage fragments of outer membrane protein CD of Branhamella catarrhalis

| Molecular mass[1] predicted from gene sequence[2] | Molecular mass measured from SDS-PAGE[3] |
|---|---|
| 34,919 | ~50,000 |
| 4,408 | 4,900 |
| 3,593 | 4,000 |
| 2,450 | 2,500 |
| 358 | |

[1]Molecular masses are noted in daltons.
[2]See SEQ ID No. 14 for nucleotide sequence.
[3]SDS-PAGE: Sodium dodecyl sulfate polyacrylamide gel electrophoresis. See FIG. 6 for tricine gels.

Thus, the open reading frame identified in pCD1 represents the entire gene encoding CD and the protein behaves aberrantly in SDS-PAGE. This discrepancy between the predicted molecular mass and the molecular mass observed in SDS-PAGE appears to be due to a proline-rich region in the large cyanogen bromide fragment in the amino terminal region of the protein as a variety of other proline-rich proteins demonstrate this characteristic (Postle et al., 1983, Proc. Natl. Acad. Sci. USA 50:5235–5239; Woods et al., 1989, Mol. Microbiol. 3(1):43–48; and Thole et al., 1990, Infect. Immun. 58:80–87).

A search of sequence data bases disclosed that the sequence of the CD gene shares homology with the OprF genes of Pseudomonas species. The CD protein contains a region (amino acid 240–280) which is rich in proline, alanine and valine. This sequence shares homology with the TonB protein of E. coli and Serratia marcescens.

Embodiment E

Methods for using CD, or CD peptides, in diagnostic immunoassays.

CD protein from B. catarrhalis, or recombinant CD protein or recombinant CD peptides produced from an expression vector system, can be purified with methods known in the art including detergent extraction and/or immunoaffinity chromatography. For example, a partially purified preparation, containing primarily bacterial outer membrane proteins, can be prepared as follows. Bacteria expressing CD from 30 chocolate agar plates were scraped into 25 ml of PBS, pH 7.2, and harvested by centrifugation at 12,000×g for 20 minutes at 4° C. The bacterial pellet was resuspended in 10 ml of 1M sodium acetate-0.001M S-mercaptoethanol (pH 4.0). A 90-ml volume of a solution containing 5% Zwitterronic detergent (Zwittergent™) Z 3-14 (Calbiochem-Behring) and 0.5% M CaCL$_2$ was added, and the suspension was mixed for 1 hour at room temperature. Nucleic acids were precipitated by the addition of 25 ml cold ethanol and subsequent centrifugation at 17,000×g for 10 minutes at 4° C. The remaining proteins were precipitated by the addition of 375 ml cold ethanol and collected by centrifugation at 17,000×g for 20 minutes at 4° C. The pellets were allowed to dry and were then suspended in 10 ml of detergent buffer containing 0.05% Zwitterionic detergent (Zwittergent™) 0.05M Tris, 0.01M EDTA, pH 8.0, and mixed for 1 hour at room temperature. The bacterial outer membrane proteins are present in the soluble fraction of the detergent buffer after centrifugation at 12,000×g for 10 minutes at 4° C.

Immunopurification of the CD protein from an outer membrane protein preparation may be accomplished using methods known in the art for immunoaffinity chromatography. CD-specific monoclonal antibodies, such as 5E8 and 7D6, may be linked to a chromatographic matrix to form an affinity matrix. The outer membrane protein preparation is then incubated with the affinity matrix allowing the antibodies to bind to CD. The affinity matrix is then washed to remove unbound components and CD is then eluted from the affinity matrix resulting in a purified preparation of CD protein. The purified CD may be used as an antigen for diagnostic assays, or may be chemically or enzymatically cleaved into peptides, as illustrated in Embodiment D. Alternatively, CD peptides may be synthesized using the deduced amino acid sequence from the gene encoding CD as a reference.

Recombinant CD protein has been purified using an expression system wherein the plasmid expression vector (pGEX2T) directs the synthesis of foreign polypeptides in E. coli as a fusion protein with glutathione-S-transferase (GST), a 26 kilodalton protein from Schistosoma japonicum. In this mode of the embodiment, and using pCD2 as the template, the gene encoding CD was amplified by the polymerase chain reaction using oligonucleotides corresponding to sequences at the 5' and 3' termini of the gene. BamH1 restriction sites were included on these oligonucleotides. Amplified product from the reaction was subjected to agarose gel electrophoresis. The 1.2 kilobase band was excised from the gel and the DNA fragment was purified from the gel slice. The fragment was cut with BamHI and ligated to pGEX2T which had been cut with BamHI and treated with calf intestine phosphatase. This recombinant plasmid was then transformed into E. coli JM109. Twelve resulting colonies were immunoscreened for reactivity with CD-specific monoclonal antibody 7D6. The plasmids from the four immunoreactive clones were purified, and subjected to agarose gel electrophoresis to determine if they had inserts of the appropriate size. To purify the CD protein, one of the immunoreactive clones was grown in 400 ml of LB broth containing 25 µg/ml of ampicillin by adding forty ml of an overnight culture to 360 ml of broth, and incubating for 1.5 hours at 37° C. with shaking. IPTG was added to 0.01 mM and the culture was incubated for an additional 3 hours. Cells were centrifuged at 5000×g and the cell pellet was resuspended in 5 ml of PBS. Cells were sonicated and the mixture was centrifuged at 10,000×g for 10 minutes. The supernatant was mixed with 0.5 ml of preswelled glutathione-agarose beads. After mixing for 2 minutes at room temperature, the beads (with fusion protein bound to the glutathione) were washed 2 additional times with PBS containing 1% non-ionic detergent (Triton®X-100). The beads were then washed once in 0.05M Tris, pH 8.0. To cleave the CD protein from the glutathione-S-transferase, the washed beads were incubated in 0.025% (final concentration) human thrombin in Tris buffer for 1 hour at room temperature. A protease inhibitor, PMSF, was then added to a concentration of 100 µg/ml. The beads were removed by centrifugation and the supernatant was examined for purified CD protein by subjecting a portion of the supernatant to SDS-PAGE. The polyacrylamide gel, stained with Coomassie blue, revealed a single band at an apparent molecular mass of 60 kilodaltons representing purified recombinant CD protein. Immunoblot assay affirmed that the band was reactive with CD-specific monoclonal antibody 7D6, and that the band is identical in mass to native CD protein contained in an adjacent lane.

Purified CD protein and CD peptides may be used as antigens in immunoassays for the detection of *Branhamella catarrhalis*-specific antisera present in the body fluid of an individual suspected of having an infection caused by *B. catarrhalis*. The body fluids include, but are not limited to, middle ear fluid, sputum, blood, and fluids from the nasopharynx, eye, and adenoid. The detection of CD or CD peptides as an antigen in immunoassays, includes any immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

Embodiment F

Methods and compounds for vaccine formulations related to CD and peptides.

This embodiment of the present invention is to provide CD protein and/or peptides thereof, to be used in as immunogens in a vaccine for active immunization to protect against infections caused by *B. catarrhalis*. In a study of the human immune response to outer membrane proteins of *B. catarrhalis,* 11 of 13 patients with well-documented infections caused by *B. catarrhalis* had IgG to CD in their convalescent sera (unpublished). The 13 patients included 6 children with otitis media and 7 adults with bronchopulmonary infections due to *B. catarrhalis*.

Thus for vaccine development, the CD protein may be purified from *B. catarrhalis* or may be purified from a host containing a recombinant vector which expresses CD or CD peptides. Such hosts include, but are not limited to, bacterial transformants, yeast transformants, filamentous fungal transformants, and cultured cells that have been either infected or transfected with a vector which encodes CD or peptides. Peptides corresponding to portions of the CD protein may be produced from chemical or enzymatic cleavage of CD protein (See for example, Embodiment D); or chemically synthesized using methods known in the art and with the amino acid sequence deduced from the nucleotide sequence of the gene encoding CD as a reference. Alternatively, CD peptides may be produced from a recombinant vector (See for example, Embodiment A). The protein or peptide immunogen is included in the subunit vaccine formulation in therapeutically effective amounts to induce an immune response. The subunit vaccine may further comprise a physiological carrier such as a solution, a polymer or liposomes; and an adjuvant, or a combination thereof.

Another mode of this embodiment provides for either a live recombinant viral vaccine, or an inactivated recombinant viral vaccine which is used to protect against infections caused by *B. catarrhalis*. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as CD, or CD peptides, thereby providing long-lasting immunity.

To illustrate this mode of the embodiment, using molecular biological techniques such as those illustrated in Embodiment A, the gene encoding CD, or a gene fragment encoding one or more CD peptides, may be inserted into the vaccinia virus genomic DNA at a site which allows for expression of CD epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen.

As an alternative to active immunization, such as where an immunocompromised individual is suffering from a potentially life-threatening infection caused by *B. catarrhalis,* immunization may be passive, i.e. immunization comprising administration of purified human immunoglobulin containing antibody against CD epitopes.

It should be understood that while the invention has been described in detail herein, the examples were for illustrative purposes only. Other modifications of the embodiments of the present invention that are obvious to those skilled in the art of molecular biology, medical diagnostics, and related disciplines are intended to be within the scope of the appended claims.

I claim:

1. A composition, for detection of *Branhamella catarrhalis* in a clinical specimen, consisting essentially of a purified and isolated oligonucleotide, said oligonucleotide consists of a nucleic acid sequence which (a) consists of from about 15 nucleotides to about 20 nucleotides in a sequence selected from a gene designated by nucleotide position 88 to nucleotide position 1446 of SEQ ID No. 14 or said gene's complementary strand;

(b) has a cytosine and guanine content which is lower than adenosine and thymidine content; and (c) has been synthesized to complement and specifically hybridize to regions of said gene or its complementary strand.

2. The composition according to claim 1, wherein the oligonucleotide consists of a nucleic acid sequence selected from the group consisting of SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 15, SEQ ID No. 16, SEQ ID No. 17, or SEQ ID No. 18.

3. A method for detecting the presence or absence of *Branhamella catarrhalis* in a clinical specimen, wherein the method comprises the steps of:

(a) obtaining a specimen of body fluid;

(b) lysing *B. catarrhalis* cells that may be present in the specimen to release bacterial genetic material;

(c) contacting said genetic material that may be present from step (b) with an oligonucleotide probe consisting of a composition according to claim 1 under suitable conditions permitting hybridization of the oligonucleotide to said genetic material; and (d) detecting an interaction between the genetic material, if present in said specimen, and the oligonucleotide probe, wherein the presence of said interaction correlates to the presence of *B. catarrhalis* in the specimen.

4. The method according to claim 3, wherein the oligonucleotide probe consists of a nucleic acid sequence selected from the group consisting of SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 15, SEQ ID No. 16, SEQ ID No. 17, or SEQ ID No. 18.

5. A composition for detection of *Branhamella catarrhalis*, consisting essentially of a purified and isolated oligonucleotide, said oligonucleotide consists of a nucleic acid sequence selected from the group consisting of SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 15, SEQ ID No. 16, SEQ ID No. 17, or SEQ ID No. 18.

6. A method for detecting the presence or absence of *Branhamella catarrhalis* in a clinical specimen, wherein the method comprises the steps of:

(a) obtaining a specimen of body fluid;

(b) lysing *B. catarrhalis* cells that may be present in the specimen to release bacterial genetic material;

(c) contacting said genetic material that may be present from step (b) with an oligonucleotide probe consisting of a composition according to claim 5 under suitable conditions permitting hybridization of the oligonucleotide to said genetic material; and (d) detecting an interaction between the genetic material, if present in said specimen, and the oligonucleotide probe, wherein the presence of said interaction correlates to the presence of *B. catarrhalis* in the specimen.

7. The method of claim 6, wherein the specimen is a body fluid selected from the group consisting of middle ear fluid; sputum; blood; and fluids from the nasopharynx, or eye, or adenoid.

8. A method for detecting the presence or absence of *Branhamella catarrhalis* in a clinical specimen, wherein the method comprises the steps of:

(a) lysing *B. catarrhalis* cells that may be present in the specimen to release bacterial genetic material;

(b) contacting said genetic material that may be present from step (a) with two purified oligonucleotides under suitable conditions permitting hybridization of the oligonucleotides to said genetic material, wherein a first oligonucleotide is a sequence derived from a gene strand contained within the nucleotide sequence of SEQ ID No. 14 and said first oligonucleotide consists of a sequence selected from the group of consisting of SEQ ID No. 2, SEQ ID No. 3, SEQ ID No. 5, SEQ ID No. 7, SEQ ID No. 10, SEQ ID No. 12, SEQ ID No. 13, SEQ ID No. 16, and SEQ ID No. 18; and a second oligonucleotide is a sequence derived from a strand complementary to said gene strand and said second oligonucleotide consists of a sequence selected from the group of consisting of SEQ ID No. 4, SEQ ID No. 6, SEQ ID No. 8, SEQ ID No. 9, SEQ ID No. 11, SEQ ID No. 15, and SEQ ID No. 17;

(c) enzymatically amplifying a specific region of sequence of said genetic material, that may be present, comprising the gene strand and complementary strand using the first and second oligonucleotides of step (b) as primers; and (d) detecting the presence of amplified sequences of the gene strand and complementary strand, wherein the presence of these amplified sequences correlates to the presence of *B. catarrhalis* in the specimen.

9. The method of claim 8, wherein the detection is further facilitated by hybridization of amplified sequences with a labeled oligonucleotide probe consisting of a nucleotide sequence corresponding to a region in the specific region of sequence to be amplified, said label is a label known to be incorporated in oligonucleotides selected particularly from among radioactive label, such as $^{32}$p, and enzymatic label, such as biotin.

10. The method of claim 8, wherein the specimen is a body fluid selected from the group consisting of middle ear fluid; sputum; blood; and fluids from the nasopharnyx, or eye, or adenoid.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 387 nucleotides
        ( B ) TYPE: nucleic acid
        ( C ) STRANDEDNESS: double- stranded
        ( D ) TOPOLOGY: linear ( i i ) MOLECULE TYPE: genomic DNA ( i i i ) HYPOTHETICAL: yes ( i v ) IMMEDIATE SOURCE:
        ( A ) LIBRARY: genomic
        ( B ) CLONE: lambda gt11 clone ( v ) ORIGINAL SOURCE:
  ( A ) ORGANISM: *Branhamella catarrhalis*
  ( B ) STRAIN: 25240
  ( C ) CELL TYPE: bacterium ( v i ) FEATURE:
  ( A ) LOCATION: CD gene region, 775- 1160
  ( B ) IDENTIFICATION METHOD: by experiment
  ( C ) OTHER INFORMATION: contains sequence encoding epitopes
        recognized by CD-specific ( v i i ) SEQUENCE DESCRIPTION: SEQ ID NO: 1:

| GCT | GGT | TTA | GAG | GTA | ACT | TTG | GGT | GGT | CGT | TTG | GCA | GCT | GCA | 42 |
|---|---|---|---|---|---|---|---|---|---|---|---|---|---|---|
| Ala | Gly | Leu | Glu | Val | Thr | Leu | Gly | Gly | Arg | Leu | Ala | Pro | Ala | |
| 1 | | | | 5 | | | | | 10 | | | | | |

| GTA | CCA | GTA | GCA | CCA | GTG | GCA | GAA | CCT | GTT | GCT | GAA | CCA | GTT | 84 |
|---|---|---|---|---|---|---|---|---|---|---|---|---|---|---|
| Val | Pro | Val | Ala | Pro | Val | Ala | Glu | Pro | Val | Ala | Glu | Pro | Val | |
| 15 | | | | | 20 | | | | | 25 | | | | |

| GTT | GCT | CCA | GCA | CCT | GTG | ATC | CTT | CCT | AAA | CCA | GAA | CCT | GAG | 126 |
|---|---|---|---|---|---|---|---|---|---|---|---|---|---|---|
| Val | Ala | Pro | Ala | Pro | Val | Ile | Leu | Pro | Lys | Pro | Glu | Pro | Glu | |
| | 30 | | | | | 35 | | | | | 40 | | | |

| CCT | GTC | ATT | GAG | GAA | GCA | CCA | GCT | GTA | ATT | GAA | GAT | ATT | GTT | 168 |
|---|---|---|---|---|---|---|---|---|---|---|---|---|---|---|
| Pro | Val | Ile | Glu | Glu | Ala | Pro | Ala | Val | Ile | Glu | Asp | Ile | Val | |
| | | 45 | | | | | 50 | | | | | 55 | | |

| GTT | GAT | TCA | GAC | GGA | GAT | GGT | GTG | CCT | GAT | CAT | CTG | GAT | GCC | 210 |
|---|---|---|---|---|---|---|---|---|---|---|---|---|---|---|
| Val | Asp | Ser | Asp | Gly | Asp | Gly | Val | Pro | Asp | His | Leu | Asp | Ala | |
| | | | 60 | | | | | 65 | | | | | 70 | |

| TGC | CCA | GGA | ACT | CCA | GTA | AAC | ACT | GTT | GTT | GAT | CCA | CGC | GGT | 252 |
|---|---|---|---|---|---|---|---|---|---|---|---|---|---|---|
| Cys | Pro | Glu | Thr | Pro | Val | Asn | Thr | Val | Val | Asp | Pro | Arg | Gly | |
| | | | | 75 | | | | | 80 | | | | | |

| TGC | CCA | GTA | CAG | GTT | AAT | TTG | GTA | GAA | GAG | CTT | CGC | CAA | GAG | 294 |
|---|---|---|---|---|---|---|---|---|---|---|---|---|---|---|
| Cys | Pro | Val | Gln | Val | Asn | Leu | Val | Glu | Glu | Leu | Arg | Gln | Glu | |
| 85 | | | | | 90 | | | | | 95 | | | | |

| TTG | CGT | GTA | TTC | TTT | GAT | TAT | GAT | AAA | TCA | ATC | ATC | AAA | CCA | 336 |
|---|---|---|---|---|---|---|---|---|---|---|---|---|---|---|
| Leu | Arg | Val | Phe | Phe | Asp | Tyr | Asp | Lys | Ser | Ile | Ile | Lys | Pro | |
| | 100 | | | | | 105 | | | | | 110 | | | |

| CAA | TAC | CGT | GAA | GAA | GTT | GCT | AAG | GTT | GCT | GCG | CAA | ATG | CGT | 378 |
|---|---|---|---|---|---|---|---|---|---|---|---|---|---|---|
| Gln | Tyr | Arg | Glu | Glu | Val | Ala | Lys | Val | Ala | Ala | Gln | Met | Arg | |
| | | 115 | | | | | 120 | | | | | 125 | | |

| GAA | TTC | CCA | 387 |
|---|---|---|---|
| Glu | Phe | Pro | |
| | | 129 | |

( 2 ) INFORMATION FOR SEQ ID NO:2:

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) ORIGINAL SOURCE:
    ( A ) ORGANISM: *Branhamella catarrhalis*
    ( B ) STRAIN: 25240

( i i i ) FEATURE:
    ( A ) LOCATION: CD gene region, 1116- 1135
    ( B ) IDENTIFICATION METHOD: by experiment
    ( C ) OTHER INFORMATION: hybridizes to *Branhamella catarrhalis*
          gene region ( i v ) SEQUENCE DESCRIPTION: SEQ ID NO: 2:

CCGTGAAGAA GTTGCTAAGG    20

( 2 ) INFORMATION FOR SEQ ID NO:3:

( i ) SEQUENCE CHARACTERISTICS:

(A) LENGTH: 15 nucleotides
(B) TYPE: nucleic acid
(C) STRANDEDNESS: single-stranded
(D) TOPOLOGY: linear (ii) ORIGINAL SOURCE:
(A) ORGANISM: *Branhamella catarrhalis*
(B) STRAIN: 25240

(iii) FEATURE:
(A) LOCATION: CD gene region, 206-220
(B) IDENTIFICATION METHOD: by experiment
(C) OTHER INFORMATION: hybridizes to *Branhamella catarrhalis* gene region (iv) SEQUENCE DESCRIPTION: SEQ ID NO: 3:

CTGACGAAGT CCACA    15

(2) INFORMATION FOR SEQ ID NO:4:

(i) SEQUENCE CHARACTERISTICS:
(A) LENGTH: 16 nucleotides
(B) TYPE: nucleic acid
(C) STRANDEDNESS: single-stranded
(D) TOPOLOGY: linear (ii) ORIGINAL SOURCE:
(A) ORGANISM: *Branhamella catarrhalis*
(B) STRAIN: 25240

(iii) FEATURE:
(A) LOCATION: CD gene region (complementary strand), 316-331
(B) IDENTIFICATION METHOD: by experiment
(C) OTHER INFORMATION: hybridizes to *Branhamella catarrhalis* gene region (iv) SEQUENCE DESCRIPTION: SEQ ID NO: 4:

CACCAGTCCA TAGCTC    16

(2) INFORMATION FOR SEQ ID NO:5:

(i) SEQUENCE CHARACTERISTICS:
(A) LENGTH: 16 nucleotides
(B) TYPE: nucleic acid
(C) STRANDEDNESS: single-stranded
(D) TOPOLOGY: linear (ii) ORIGINAL SOURCE:
(A) ORGANISM: *Branhamella catarrhalis*
(B) STRAIN: 25240

(iii) FEATURE:
(A) LOCATION: CD gene region, 468-483
(B) IDENTIFICATION METHOD: by experiment
(C) OTHER INFORMATION: hybridizes to *Branhamella catarrhalis* gene region (iv) SEQUENCE DESCRIPTION: SEQ ID NO: 5:

GATTGGTACT GAGCAG    16

(2) INFORMATION FOR SEQ ID NO:6:

(i) SEQUENCE CHARACTERISTICS:
(A) LENGTH: 18 nucleotides
(B) TYPE: nucleic acid
(C) STRANDEDNESS: single-stranded
(D) TOPOLOGY: linear (ii) ORIGINAL SOURCE:
(A) ORGANISM: *Branhamella catarrhalis*
(B) STRAIN: 25240

(iii) FEATURE:
(A) LOCATION: CD gene region (complementary strand), 561-578

(B) IDENTIFICATION METHOD: by experiment
(C) OTHER INFORMATION: hybridizes to *Branhamella catarrhalis* gene region ( i v ) SEQUENCE DESCRIPTION: SEQ ID NO: 6:

GTATAACCAT CAATTGCA     18

( 2 ) INFORMATION FOR SEQ ID NO:7:

( i ) SEQUENCE CHARACTERISTICS:
(A) LENGTH: 15 nucleotides
(B) TYPE: nucleic acid
(C) STRANDEDNESS: single-stranded
(D) TOPOLOGY: linear ( i i ) ORIGINAL SOURCE:
(A) ORGANISM: *Branhamella catarrhalis*
(B) STRAIN: 25240

( i i i ) FEATURE:
(A) LOCATION: CD gene region, 724-738
(B) IDENTIFICATION METHOD: by experiment
(C) OTHER INFORMATION: hybridizes to *Branhamella catarrhalis* gene region ( i v ) SEQUENCE DESCRIPTION: SEQ ID NO: 7:

GCCCGTGCTA TCCAT     15

( 2 ) INFORMATION FOR SEQ ID NO:8:

( i ) SEQUENCE CHARACTERISTICS:
(A) LENGTH: 17 nucleotides
(B) TYPE: nucleic acid
(C) STRANDEDNESS: single-stranded
(D) TOPOLOGY: linear ( i i ) ORIGINAL SOURCE:
(A) ORGANISM: *Branhamella catarrhalis*
(B) STRAIN: 25240

( i i i ) FEATURE:
(A) LOCATION: CD gene region (complementary strand), 826-842
(B) IDENTIFICATION METHOD: by experiment
(C) OTHER INFORMATION: hybridizes to *Branhamella catarrhalis* gene region ( i v ) SEQUENCE DESCRIPTION: SEQ ID NO: 8:

GGTTCTGCCA CTGGTGC     17

( 2 ) INFORMATION FOR SEQ ID NO:9:

( i ) SEQUENCE CHARACTERISTICS:
(A) LENGTH: 15 nucleotides
(B) TYPE: nucleic acid
(C) STRANDEDNESS: single-stranded
(D) TOPOLOGY: linear ( i i ) ORIGINAL SOURCE:
(A) ORGANISM: *Branhamella catarrhalis*
(B) STRAIN: 25240

( i i i ) FEATURE:
(A) LOCATION: CD gene region (complementary strand), 1211-1225
(B) IDENTIFICATION METHOD: by experiment
(C) OTHER INFORMATION: hybridizes to *Branhamella catarrhalis* gene region ( i v ) SEQUENCE DESCRIPTION: SEQ ID NO: 9:

TGTAGCGTGC ACTTG     15

( 2 ) INFORMATION FOR SEQ ID NO:10:

( i ) SEQUENCE CHARACTERISTICS:
        ( A ) LENGTH: 18 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: *Branhamella catarrhalis*
        ( B ) STRAIN: 25240

( i i i ) FEATURE:
        ( A ) LOCATION: CD gene region, 1387- 1404
        ( B ) IDENTIFICATION METHOD: by experiment
        ( C ) OTHER INFORMATION: hybridizes to *Branhamella catarrhalis*
            gene region ( i v ) SEQUENCE DESCRIPTION: SEQ ID NO: 10:

GCAGTAATCA CTGGTAGC    18

( 2 ) INFORMATION FOR SEQ ID NO:11:

( i ) SEQUENCE CHARACTERISTICS:
        ( A ) LENGTH: 15 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: *Branhamella catarrhalis*
        ( B ) STRAIN: 25240

( i i i ) FEATURE:
        ( A ) LOCATION: CD gene region (complementary strand), 1483-1497
        ( B ) IDENTIFICATION METHOD: by experiment
        ( C ) OTHER INFORMATION: hybridizes to *Branhamella catarrhalis*
            gene region ( i v ) SEQUENCE DESCRIPTION: SEQ ID NO: 11:

TCGATAAGGC TTGAG    15

( 2 ) INFORMATION FOR SEQ ID NO:12:

( i ) SEQUENCE CHARACTERISTICS:
        ( A ) LENGTH: 18 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: *Branhamella catarrhalis*
        ( B ) STRAIN: 25240

( i i i ) FEATURE:
        ( A ) LOCATION: CD gene region, 1665- 1682
        ( B ) IDENTIFICATION METHOD: by experiment
        ( C ) OTHER INFORMATION: hybridizes to *Branhamella catarrhalis*
            gene region ( i v ) SEQUENCE DESCRIPTION: SEQ ID NO: 12:

CGGGCATATC GCACGACT    18

( 2 ) INFORMATION FOR SEQ ID NO:13:

( i ) SEQUENCE CHARACTERISTICS:
        ( A ) LENGTH: 20 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: *Branhamella catarrhalis*
        ( B ) STRAIN: 25240

( i i i ) FEATURE:

(A) LOCATION: CD gene region, 941-960
(B) IDENTIFICATION METHOD: by experiment
(C) OTHER INFORMATION: hybridizes to *Branhamella catarrhalis* gene region (iv) SEQUENCE DESCRIPTION: SEQ ID NO: 13:

TTGTTGATTC AGACGGAGAT     20

(2) INFORMATION FOR SEQ ID NO:14:

(i) SEQUENCE CHARACTERISTICS:
(A) LENGTH: 1727 nucleotides
(B) TYPE: nucleic acid
(C) STRANDEDNESS: single-stranded
(D) TOPOLOGY: linear (ii) MOLECULE TYPE: genomic DNA (iii) HYPOTHETICAL: yes (iv) ORIGINAL SOURCE:
(A) ORGANISM: *Branhamella catarrhalis*
(B) STRAIN: 25240

(v) IMMEDIATE SOURCE:
(A) LIBRARY: genomic
(B) CLONE: EMBL3 clone 5
(C) SUBCLONE: pCD1

(vi) FEATURE:
(A) LOCATION: CD gene region
(B) IDENTIFICATION METHOD: by experiment
(C) NAME/KEY: signal sequence of encoded protein
(D) LOCATION: -26 to -1

(vii) SEQUENCE DESCRIPTION: SEQ ID NO: 14:

```
GGATCCCGTC  GACCTGCAGG  TCAACGGATC  GCTATGCTAA  AATAGGTGCG           50

GTAATCTTGA  AAAACCAACC  ATTCCTTGGA  GGAATTT     ATG  AAA  TTT        96
                                                Met  Lys  Phe
                                                -26

AAT  AAA  ATC  GCT  CTT  GCG  GTC  ATC  GCA  GCC  GTT  GCA  GCT  CCA  138
Asn  Lys  Ile  Ala  Leu  Ala  Val  Ile  Ala  Ala  Val  Ala  Ala  Pro
                                    -15

GTT  GCA  GCT  CCA  GTT  GCT  GCT  CAA  GCT  GGT  GTG  ACA  GTC  AGC  180
Val  Ala  Ala  Pro  Val  Ala  Ala  Gln  Ala  Gly  Val  Thr  Val  Ser
                    -5                       -1   1

CCA  CTA  CTA  CTT  GGC  TAT  CAT  TAC  ACT  GAC  GAA  GCC  CAC  AAT  222
Pro  Leu  Leu  Leu  Gly  Tyr  His  Tyr  Thr  Asp  Glu  Ala  His  Asn
 5                        10                      15

GAT  CAA  CGC  AAA  ATC  TTA  CGC  ACT  GGC  AAG  AAG  CTA  GAG  CTA  264
Asp  Gln  Arg  Lys  Ile  Leu  Arg  Thr  Gly  Lys  Lys  Leu  Glu  Leu
      20                       25                      30

GAT  GCT  ACT  AAT  GCA  CCT  GCA  CCA  GCT  AAT  GGC  GGT  GTC  GCA  306
Asp  Ala  Thr  Asn  Ala  Pro  Ala  Pro  Ala  Asn  Gly  Gly  Val  Ala
          35                      40                      45

CTG  GAC  AGT  GAG  CTA  TGG  ACT  GGT  GCT  GCG  ATT  GGT  ATC  GAA  348
Leu  Asp  Ser  Glu  Leu  Trp  Thr  Gly  Ala  Ala  Ile  Gly  Ile  Glu
               50                       55                       60

CTT  ACG  CCA  TCA  ACT  CAG  TTC  CAA  GTT  GAA  TAT  GGT  ATC  TCT  390
Leu  Thr  Pro  Ser  Thr  Gln  Phe  Gln  Val  Glu  Tyr  Gly  Ile  Ser
                    65                       70

AAC  CGT  GAT  GCA  AAA  TCT  TCA  GAC  AAA  TCT  GCA  CAT  CGC  TTT  432
Asn  Arg  Asp  Ala  Lys  Ser  Ser  Asp  Lys  Ser  Ala  His  Arg  Phe
 75                       80                       85

GAT  GCT  GAG  CAA  GAA  ACC  ATC  AGC  GGT  AAC  TTT  TTG  ATT  GGT  474
Asp  Ala  Glu  Gln  Glu  Thr  Ile  Ser  Gly  Asn  Phe  Leu  Ile  Gly
          90                      95                      100
```

| | | | | | | | | | | | | | | |
|---|---|---|---|---|---|---|---|---|---|---|---|---|---|---|
| ACT | GAG | CAG | TTC | AGC | GGC | TAC | AAT | CCA | ACA | AAT | AAA | TTC | AAG | 516 |
| Thr | Glu | Gln | Phe | Ser | Gly | Tyr | Asn | Pro | Thr | Asn | Lys | Phe | Lys | |
| | | 105 | | | | 110 | | | | | 115 | | | |
| CCC | TAT | GTC | TTG | GTT | GGT | GCA | GGT | CAA | TCT | AAA | ATT | AAA | GTA | 558 |
| Pro | Tyr | Val | Leu | Val | Gly | Ala | Gly | Gln | Ser | Lys | Ile | Lys | Val | |
| | | | 120 | | | | | 125 | | | | | 130 | |
| AAT | GCA | ATT | GAT | GGT | TAT | ACA | GCA | GAA | GTA | GCC | AAT | GGG | CAA | 600 |
| Asn | Ala | Ile | Asp | Gly | Tyr | Thr | Ala | Glu | Val | Ala | Asn | Gly | Gln | |
| | | | | 135 | | | | | 140 | | | | | |
| AAC | ATT | GCA | AAA | GAT | CAA | GCT | GTA | AAA | GCA | GGT | CAA | GAA | GTT | 642 |
| Asn | Ile | Ala | Lys | Asp | Gln | Ala | Val | Lys | Ala | Gly | Gln | Glu | Val | |
| 145 | | | | | 150 | | | | | 155 | | | | |
| GCT | GAG | TCT | AAA | GAC | ACC | ATC | GGT | AAC | CTA | GGT | CTT | GGT | GCT | 684 |
| Ala | Glu | Ser | Lys | Asp | Thr | Ile | Gly | Asn | Leu | Gly | Leu | Gly | Ala | |
| | | 160 | | | | 165 | | | | | 170 | | | |
| CGC | TAC | TTA | GTC | AAT | GAT | GCC | CTT | GCA | CTT | CGT | GGT | GAA | GCC | 726 |
| Arg | Tyr | Leu | Val | Asn | Asp | Ala | Leu | Ala | Leu | Arg | Gly | Glu | Ala | |
| | | 175 | | | | | 180 | | | | | 185 | | |
| CGT | GCT | ATC | CAT | AAT | TTT | GAT | AAC | AAA | TGG | TGG | GAA | GGC | TTG | 768 |
| Arg | Ala | Ile | His | Asn | Phe | Asp | Asn | Lys | Trp | Trp | Glu | Gly | Leu | |
| | | | 190 | | | | | 195 | | | | | 200 | |
| GCG | TTG | GCT | GGT | TTA | GAG | GTA | ACT | TTG | GGT | GGT | CGT | TTG | GCA | 810 |
| Ala | Leu | Ala | Gly | Leu | Glu | Val | Thr | Leu | Gly | Gly | Arg | Leu | Ala | |
| | | | | 205 | | | | | 210 | | | | | |
| CCT | GCA | GTA | CCA | GTA | GCA | CCA | GTG | GCA | GAA | CCT | GTT | GCT | GAA | 852 |
| Pro | Ala | Val | Pro | Val | Ala | Pro | Val | Ala | Glu | Pro | Val | Ala | Glu | |
| 215 | | | | | 220 | | | | | 225 | | | | |
| CCA | GTT | GTT | GCT | CCA | GCA | CCT | GTG | ATC | CTT | CCT | AAA | CCA | GAA | 894 |
| Pro | Val | Val | Ala | Pro | Ala | Pro | Val | Ile | Leu | Pro | Lys | Pro | Glu | |
| | | 230 | | | | | 235 | | | | | 240 | | |
| CCT | GAG | CCT | GTC | ATT | GAG | GAA | GCA | CCA | GCT | GTA | ATT | GAA | GAT | 936 |
| Pro | Glu | Pro | Val | Ile | Glu | Glu | Ala | Pro | Ala | Val | Ile | Glu | Asp | |
| | | | 245 | | | | | 250 | | | | | 255 | |
| ATT | GTT | GTT | GAT | TCA | GAC | GGA | GAT | GGT | GTG | CCT | GAT | CAT | CTG | 978 |
| Ile | Val | Val | Asp | Ser | Asp | Gly | Asp | Gly | Val | Pro | Asp | His | Leu | |
| | | | | 260 | | | | | 265 | | | | | 270 |
| GAT | GCC | TGC | CCA | GGA | ACT | CCA | GTA | AAC | ACT | GTT | GTT | GAT | CCA | 1020 |
| Asp | Ala | Cys | Pro | Gly | Thr | Pro | Val | Asn | Thr | Val | Val | Asp | Pro | |
| | | | | 275 | | | | | 280 | | | | | |
| CGC | GGT | TGC | CCA | GTA | CAG | GTT | AAT | TTG | GTA | GAA | GAG | CTT | CGC | 1062 |
| Arg | Gly | Cys | Pro | Val | Gln | Val | Asn | Leu | Val | Glu | Glu | Leu | Arg | |
| 285 | | | | | 290 | | | | | 295 | | | | |
| CAA | GAG | TTG | CGT | GTA | TTC | TTT | GAT | TAT | GAT | AAA | TCA | ATC | ATC | 1104 |
| Gln | Glu | Leu | Arg | Val | Phe | Phe | Asp | Tyr | Asp | Lys | Ser | Ile | Ile | |
| | | 300 | | | | | 305 | | | | | 310 | | |
| AAA | CCA | CAA | TAC | CGT | GAA | GAA | GTT | GCT | AAG | GTT | GCT | GCG | CAA | 1146 |
| Lys | Pro | Gln | Tyr | Arg | Glu | Glu | Val | Ala | Lys | Val | Ala | Ala | Gln | |
| | | | 315 | | | | | 320 | | | | | 325 | |
| ATG | CGT | GAA | TTC | CCA | AAT | GCA | ACT | GCA | ACC | ATT | GAA | GGT | CAC | 1188 |
| Met | Arg | Glu | Phe | Pro | Asn | Ala | Thr | Ala | Thr | Ile | Glu | Gly | His | |
| | | | | 330 | | | | | 335 | | | | | 340 |
| GCA | TCA | CGC | GAT | TCA | GCA | CGC | TCA | AGT | GCA | CGC | TAC | AAC | CAG | 1230 |
| Ala | Ser | Arg | Asp | Ser | Ala | Arg | Ser | Ser | Ala | Arg | Tyr | Asn | Gln | |
| | | | | 345 | | | | | 350 | | | | | |
| CGT | CTA | TCT | GAA | GCT | CGT | GCT | AAT | GCT | GTT | AAA | TCA | ATG | CTA | 1272 |
| Arg | Leu | Ser | Glu | Ala | Arg | Ala | Asn | Ala | Val | Lys | Ser | Met | Leu | |
| 355 | | | | | 360 | | | | | 365 | | | | |
| TCT | AAC | GAA | TTT | GGT | ATC | GCT | CCA | AAC | CGC | CTA | AAT | GCA | GTT | 1314 |
| Ser | Asn | Glu | Phe | Gly | Ile | Ala | Pro | Asn | Arg | Leu | Asn | Ala | Val | |
| | | 370 | | | | | 375 | | | | | 380 | | |

```
GGT TAT GGC TTT GAT CGT CCT ATC GCT CCA AAT ACT ACT GCT      1356
Gly Tyr Gly Phe Asp Arg Pro Ile Ala Pro Asn Thr Thr Ala
        385                 390                 395

GAA GGT AAA GCG ATG AAC CGT CGT GTA GAA GCA GTA ATC ACT      1398
Glu Gly Lys Ala Met Asn Arg Arg Val Glu Ala Val Ile Thr
            400                 405                 410

GGT AGC AAA ACA ACG ACT GTT GAT CAA ACC AAA GAT ATG ATT      1440
Gly Ser Lys Thr Thr Thr Val Asp Gln Thr Lys Asp Met Ile
                415                 420

GTT CAA TAATTGCACA TGAGTATTTG GTAATCAGCT TGAATTCTCA           1486
Val Gln
425

AGCCTTATCG ATAAAAAAGC CACCTTTTTG GTGGCTTTTT TATTTGGTGT        1536

AAATTTTTGG TTCAGTTAGA CTGATTTATG TTATAATAAG CGGTTTTCTT        1586

AGCTTTTGAA TAAATCAGAT GAGTTAAGCC AACTGACTGA TTTTATCAAT        1636

TGAGTTATTT TTAAGCCTTT TATCAGTTCG GGCATATCGC ACGACTATTA        1686

ATCTTTATAT GAGTATTTAT GGCAGACGAC ATTAAGCATT T                1727
```

( 2 ) INFORMATION FOR SEQ ID NO:15:

( i ) SEQUENCE CHARACTERISTICS:
    ( A ) LENGTH: 17 nucleotides
    ( B ) TYPE: nucleic acid
    ( C ) STRANDEDNESS: single- stranded
    ( D ) TOPOLOGY: linear ( i i ) ORIGINAL SOURCE:
    ( A ) ORGANISM: *Branhamella catarrhalis*
    ( B ) STRAIN: 25240

( i i i ) FEATURE:
    ( A ) LOCATION: CD gene region (complementary strand), 1430-1446
    ( B ) IDENTIFICATION METHOD: by experiment
    ( C ) OTHER INFORMATION: hybridizes to *Branhamella catarrhalis*
         gene region ( i v ) SEQUENCE DESCRIPTION: SEQ ID NO: 15:

TTGAACAATC ATATCTT     17

( 2 ) INFORMATION FOR SEQ ID NO:16:

( i ) SEQUENCE CHARACTERISTICS:
    ( A ) LENGTH: 18 nucleotides
    ( B ) TYPE: nucleic acid
    ( C ) STRANDEDNESS: single- stranded
    ( D ) TOPOLOGY: linear ( i i ) ORIGINAL SOURCE:
    ( A ) ORGANISM: *Branhamella catarrhalis*
    ( B ) STRAIN: 25240

( i i i ) FEATURE:
    ( A ) LOCATION: CD gene region, 166- 183
    ( B ) IDENTIFICATION METHOD: by experiment
    ( C ) OTHER INFORMATION: hybridizes to *Branhamella catarrhalis*
         gene region ( i v ) SEQUENCE DESCRIPTION: SEQ ID NO: 16:

GGTGTGACAG TCAGCCCA     18

( 2 ) INFORMATION FOR SEQ ID NO:17:

( i ) SEQUENCE CHARACTERISTICS:
    ( A ) LENGTH: 17 nucleotides
    ( B ) TYPE: nucleic acid
    ( C ) STRANDEDNESS: single- stranded

```
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region (complementary strand), 1081-1097
        ( B ) IDENTIFICATION METHOD: by experiment
        ( C ) OTHER INFORMATION: hybridizes to Branhamella catarrhalis
              gene region ( i v ) SEQUENCE DESCRIPTION: SEQ ID NO: 17:

GATTTATCAT AATCAAA          17

( 2 ) INFORMATION FOR SEQ ID NO:18:

( i ) SEQUENCE CHARACTERISTICS:
        ( A ) LENGTH: 17 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region, 1048- 1064
        ( B ) IDENTIFICATION METHOD: by experiment
        ( C ) OTHER INFORMATION: hybridizes to Branhamella catarrhalis
              gene region ( i v ) SEQUENCE DESCRIPTION: SEQ ID NO: 18:

GTAGAAGAGC TTCGCCA          17
```